United States Patent
Breeuwer et al.

(10) Patent No.: US 10,123,721 B2
(45) Date of Patent: Nov. 13, 2018

(54) DETERMINATION OF PHYSIOLOGICAL PARAMETERS OF TISSUE FROM DYNAMIC CONTRAST-ENHANCED MR DATA

(71) Applicant: KONINKLIJKE PHILIPS N.V., Eindhoven (NL)

(72) Inventors: Marcel Breeuwer, Eindhoven (NL); Massimo Mischi, Eindhoven (NL); Hessel Wijkstra, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 522 days.

(21) Appl. No.: 14/781,402

(22) PCT Filed: Mar. 27, 2014

(86) PCT No.: PCT/IB2014/060221
§ 371 (c)(1),
(2) Date: Sep. 30, 2015

(87) PCT Pub. No.: WO2014/162246
PCT Pub. Date: Oct. 9, 2014

(65) Prior Publication Data
US 2016/0022169 A1    Jan. 28, 2016

Related U.S. Application Data

(60) Provisional application No. 61/807,806, filed on Apr. 3, 2013.

(51) Int. Cl.
*A61B 5/055* (2006.01)
*A61B 5/026* (2006.01)
*G01R 33/56* (2006.01)
*G01R 33/563* (2006.01)
*G06F 19/00* (2018.01)

(52) U.S. Cl.
CPC ............ *A61B 5/055* (2013.01); *A61B 5/0263* (2013.01); *G01R 33/5601* (2013.01); *G01R 33/56341* (2013.01); *G06F 19/00* (2013.01)

(58) Field of Classification Search
CPC .................. A61B 5/055; A61B 5/0263; G01R 33/56341; G01R 33/5601
See application file for complete search history.

(56) References Cited

U.S. PATENT DOCUMENTS

2007/0167731 A1* 7/2007 Taxt ................... G01R 33/5601
                                                                600/410
2011/0257519 A1    10/2011 Bjrerud

OTHER PUBLICATIONS

Ludemann et al, "Simultaneous Quantification of Perfusion and Permeability in the Prostate Using Dynamic Contrast-Enhanced . . . " Annals of Biomedical Engineering, vol. 37, No. 4, Apr. 2009, p. 749-762.

(Continued)

*Primary Examiner* — Peter Luong

(57) ABSTRACT

A method of determining microvascular architecture is disclosed. Dynamic contrast-enhanced magnetic resonance data acquired from a contrast agent administered to at least a part of a subject to be examined. From the dynamic contrast-enhanced magnetic resonance data a leakage parameter ($k_{ep}$) and a dispersion parameter (k) are computed. Effects of both convective dispersion and extravasation kinetics of contrast agent are taken into account.

9 Claims, 4 Drawing Sheets

(56) References Cited

OTHER PUBLICATIONS

Bonekamp et al, "Dynamic Contrast Enhanced Magnetic Resonance Imaging in the Evaluation of the Prostate" Top Magn. Reson. Imaging, vol. 19, No. 6, Dec. 2008, p. 273-284.
Sourbron et al, "Tracer Kinetic Modelling in MRS: Estimating Perfusion and Capillary Permeability" Phys. Med. Biol. 57, (2012).
Mischi et al "Angiogenesis Imaging by Spatiotemporal Analysis of Ultrasound Contract Agent Dispersion Kinetics" IEEE Transactions on Ultrasonics, Ferroelectrics and Frequency Control, vol. 59, No. 4, Apr. 2012, p. 621.
Tofts et al "Estimating Kinetic Parameters from Dynamic Contrast-Enhanced Ti-Weighted . . . "Journal of Magnetic Resonance Imaging 10, (1999) p. 223-232.
Taylor, G., "Dispersion of soluble matter in solvent flowing slowly through a tube" Proc. R. Soc. Lond, 1953. 219(1137): p. 186-203.
Mischi, M., "Contrast echocardiography for cardiac quantifications" 2004, Eindhoven University of Technology: Eindhoven. Oct. 4, 2004.
Tofts, P.S. and A.G. Kermode, "Measurement of the blood-brain barrier permeability and leakage space using dynamic MR imaging. 1. Fundamental concepts" Magn Reson Med, 1991. 17(2): p. 357-67.
Parker, G.J. et al., "Experimentally-derived functional form for a population-averaged high-temporal-resolution arterial input function for dynamic contrast-enhanced MRI" Magn Reson Med, 2006. 56(5): p. 993-1000.
Kuenen, M.P., M. Mischi, and H. Wijkstra, "Contrast-ultrasound diffusion imaging for localization of prostate cancer" IEEE Trans Med Imaging, 2011. 30(8): p. 1493-502.
Vonken, E.J., et al., "Measurement of cerebral perfusion with dual-echo multi-slice quantitative dynamic susceptibility contrast MRI" J Magn Reson Imaging, 1999. 10(2): p. 109-17.
Kompatsiari, "Quatitative Angiogenesis Imaging in Prostate Cancer by DCE MR Dispersion Imaging" Aug. 2012, Eindhoven Univeristy of Technology.
M. Mischi et al, "Contrast Dispersion Mapping in DCE MRI . . . " ISMRM 2013 abstract Apr. 4, 2013.

\* cited by examiner

DETERMINATION OF PHYSIOLOGICAL PARAMETERS OF TISSUE FROM DYNAMIC CONTRAST-ENHANCED MR DATA

CROSS REFERENCE TO RELATED APPLICATIONS

This application is a U.S. national phase application of International Application No. PCT/2014/060221, filed on Mar. 27, 2014, which claims the benefit of U.S. provisional Application Ser. No. 61/807,806 filed on Apr. 3, 2013 and is incorporated herein by reference.

FIELD OF THE INVENTION

The invention pertains to a method to determine physiological parameters of tissue from dynamic contrast-enhanced image data, notably MR data.

BACKGROUND OF THE INVENTION

Determination of micro-vascular architecture is known from the paper '*Estimating Kinetic Parameters From Dynamic Contrast-Enhanced T1-Weighted MRI of a Diffusible Tracer: Standardized Quantities and Symbols*' by Paul S. Tofts, et al in Journal of magnetic resonance imaging 10:223-232 (1999).

The known method employs a dynamic contrast-enhanced T1-weighted magnetic resonance imaging method. The magnetic resonance signals from a region of interest can give information about blood flow, capillary leakage and related physiological parameters. From the acquired image data kinetic parameters such as the flux rate between extravascular extracellular space and plasma are computed.

SUMMARY OF THE INVENTION

An object of the present invention is to determine microvascular architecture of tissue from dynamic contrast-enhanced magnetic resonance signals.

This object is achieved according to the invention by the method of determining microvascular architecture from dynamic contrast-enhanced image data, notably dynamic contrast-enhanced magnetic resonance data, acquired from a contrast agent administered to at least a part of a subject to be examined, wherein from the dynamic contrast-enhanced magnetic resonance data a leakage parameter (kep) and a dispersion parameter ($\kappa$) are computed taking into account effects of both convective dispersion and extravasation kinetics of contrast agent.

DESCRIPTION OF THE INVENTION

The invention employs dynamic contrast-enhanced image data acquired from a patient to be examined to which a contrast agent has been administered or an endogenous contrast agent is employed. The contrast enhanced image data may be notably contrast enhanced magnetic resonance data, while also contrast enhanced (x-ray) computed tomography, rotational x-ray (angiographic) imaging or contrast-enhanced ultrasound may be employed to generate the contrast-enhanced image data from which the micro-vascular architecture is derived.

According to the invention the leakage parameter and the dispersion parameter that characterize micro-vascular architecture and permeability are computed from the contrast-enhanced image data, e.g. magnetic resonance data. The convective dispersion represents intravascular transport kinetics of the contrast agents as it progresses through the blood vessels on the subject under examination. The dispersion parameter appears to be good indicator for characterizing angiogenesis and hence the presence of cancerous tissue. The dispersion parameter $\kappa$ represents the local ratio between the squared carrier velocity (due to convention) and the (apparent) dispersion coefficient. This is notably attributed to the role of vascular tortuosity which correlates well with increase in angiogenic micro-vessels. Higher tortuosity acts against dispersion, so that the contrast agent is constraint in space and the dispersion time increases.

An insight of the present invention is that leakage of the contrast agent out of the blood vessels into the extravascular tissue provides a major contribution to the transport dynamics of the contrast agent concentration, a more accurate and reliable result for the dispersion parameter is obtained. Moreover, according to the present invention, no estimation or measurement of the arterial input function is required. The present invention further enables simultaneous computation of the leakage parameter and the dispersion parameter.

In one aspect of the invention the convective dispersion is modeled by fitting the time concentration curve to a modified local density random walk model. In this way the convective dispersion effects are taken into account by solving the convective dispersion of the contrast agent. Further, approximation of the travelling bolus of contrast agent by a normal (i.e. Gaussian) spatial distribution appears an accurate representation. This approximation provides an algebraic solution and reduces computational burden.

In a further aspect of the invention contribution of the capillary compartment to the measured contrast-enhanced magnetic resonance data is neglected. This leads to a simplified dispersion model.

In yet another aspect of the invention, a simple mono-compartment representation of leakage is employed. Then the leakage parameter can be simply computed as the ratio of the extravascular-leakage time constant and the fractional volume of the extravascular space.

The invention further pertains to a data processing system and a computer program for determining microvascular architecture from dynamic contrast-enhanced magnetic resonance data. A computer program is disclosed for determining microvascular architecture from dynamic contrast-enhanced magnetic resonance data acquired from a contrast agent administered to at least a part of a subject to be examined. The computer program comprises instructions which when run on a computer compute from the dynamic contrast-enhanced magnetic resonance data a leakage parameter ($k_{ep}$) and a dispersion parameter ($\kappa$) taking into account effects of both convective dispersion and extravasation kinetics of contrast agent. A data processing system has hardware and software configured for determining microvascular architecture from dynamic contrast-enhanced magnetic resonance data acquired from a contrast agent administered to at least a part of a subject to be examined. The data processing system is configured to compute from the dynamic contrast-enhanced magnetic resonance data a leakage parameter ($k_{ep}$) and a dispersion parameter ($\kappa$) taking into account effects of both convective dispersion and extravasation kinetics of contrast agent. The computer program of the invention can be provided on a data carrier such as a CD-ROM disk or a USB memory stick, or the computer program of the invention can be downloaded from a data network such as the world-wide web. When installed in the computer included in a magnetic resonance imaging system the magnetic resonance imaging system is enabled to operate according to the invention.

The result of the method of the invention is a quantitative analysis of the microvascular structure of the patient to be examined. This quantitative result is a technical intermediate result which can be employed by a physician to assess the state of the vascularity of the region of the patient to be examined.

These and other aspects of the invention will be elucidated with reference to the embodiments described hereinafter and with reference to the accompanying drawing wherein FIG. 1. shows, from left to right, prostate images by T2, weighted diffusion, and DCE MRI;

DETAILED DESCRIPTION OF THE EMBODIMENTS

Figure 1:
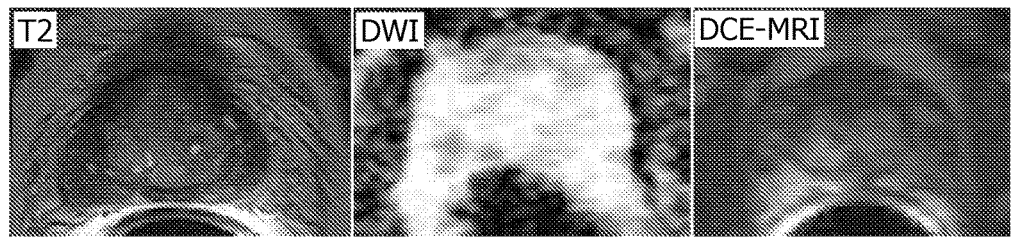

This invention addresses the feasibility of dispersion imaging by DCE MRI is investigated for the first time. Intravascular dispersion is assessed by fitting the modified Local Density Random Walk (mLDRW) model to the measured TCCs. This model is a solution of the convective dispersion equation assuming a Normal distribution of the contrast bolus in space prior to the bolus passage through each detection voxel. More precisely, the estimated intravascular dispersion parameter, $\kappa = v^2/D$, represents the local ratio between contrast convection (squared velocity $v^2$) and dispersion (D). Dispersion, represented by the dispersion coefficient D in the convective dispersion equation, is affected by concurrent processes, comprising molecular diffusion, flow profile, and transit time distribution due to the multipath trajectories defined by the microvascular network. In the microvasculature, the latter term is dominant, and dispersion may represent a valuable option to characterize the microvascular architecture.

While the mLDRW model can directly be applied when blood pool agents are used, it is preferred in view of the presence of extravascular leakage to separate the intravascular from the extravascular phase. To this end, the mLDRW model is integrated in the two-compartment Tofts model and is used to represent the intravascular blood plasma compartment. The two-compartment differential equation is then integrated leading to a new holistic model whose parameters permit the assessment of both dispersion $\kappa$ and permeability $k_{ep}$. Due to the large parameterization, comprising six parameters, the achievement of accurate parameter estimation is challenging. Therefore, a simplified dispersion model is also proposed where the contribution of the capillary compartment to the measured signal is neglected, reducing the model parameterization to five parameters.

Due to its relevance and incidence, PCa is chosen to test the clinical feasibility of the proposed methods. In the United States, PCa accounts for 28% and 10% of all cancer diagnoses and deaths in males, respectively. Despite the availability of efficient focal therapies, their timely and efficient use is hampered by a lack of reliable imaging methods for timely localization of prostate cancer. The use of multi-parametric (mp) MRI, usually combining standard $T_2$, permeability, and diffusion-weighted MRI, has been proposed as a possible valid option for PCa imaging. However, proper application and interpretation of mpMRI remains a complex procedure, requiring the involvement of expert centers. As a result, current clinical diagnosis of PCa is still based on repeated systematic biopsies.

The proposed methods were evaluated with ten patients diagnosed with prostate cancer and referred for a radical prostatectomy. After the intravenous injection of a bolus of gadolinium-DPTA, time concentration curves were measured at each pixel and fitted by the proposed models to generate permeability and dispersion maps. Diffusion-weighted MRI, leading to parametric maps of (water) apparent diffusion coefficient (ADC), was also performed and used for comparison. The proposed methods were evaluated for their capability to distinguish between cancerous and healthy tissue on a pixel basis. The ground truth was represented by the histological results after radical prostatectomy.

Theory

Intravascular Dispersion

Convective dispersion describes the process of an indicator bolus transported by a flowing carrier fluid. The bolus distribution in space evolves over time driven by two main phenomena, namely, convection and dispersion. Convection represents the translation of the bolus spatial distribution due to the drag force of the carrier fluid. In most clinical application, the convection velocity is assumed to be equal to the carrier fluid velocity. In general, dispersion represents the Brownian motion of the indicator due to molecular diffusion, driven by heat and concentration gradient [b]. However, in the presence of convection phenomena, dispersion is dominated by fluid-dynamic effects such as flow profile in larger vessels, or multipath trajectories in the microcirculation. The combination of all the above mentioned contributions to dispersion was addressed as apparent dispersion by G.I. Taylor [a]. The equation describing convective dispersion phenomena, simplified in one dimension, is given as $$\frac{\partial}{\partial t}C(x,t) = D\frac{\partial^2}{\partial x^2}C(x,t) - v\frac{\partial}{\partial x}C(x,t) \quad [1]$$

with x and t representing space and time, respectively, v being the carrier velocity, and D being the apparent dispersion coefficient, from now on referred to as dispersion coefficient. In Eq. [1], D is assumed to be time invariant and locally constant.

A solution of Eq. [1] is given by the Local Density Random Walk model which is known per se from refs [b,c]. In order to obtain a solution whose dispersion-related parameter represents the local characteristics at the measurement site, independent of the bolus history between injection and detection sites, Kuenen et al. [f] have recently proposed a modified solution of the convective dispersion equation, referred to as modified LDRW (mLDRW) model. The boundary conditions for the mLDRW solution reduce to the assumption of a Normal spatial distribution of the travelling bolus prior to entering the detection site. The mLDRW model is given as $$C(t) = \alpha \sqrt{\frac{\kappa}{2\pi(\tau - t_0)}} e^{-\frac{\kappa(\tau-t_0-\mu)^2}{2(\tau-t_0)}}. \quad [2]$$

In Eq. [2], the parameter $t_0$ represents the theoretical injection time under the assumption of constant hemodynamic conditions along the full path from the injection to the detection site represented by the local characteristics at the detection site, the parameter $\mu$ represents the mean transit time of the indicator bolus between the injection and detection site (assuming the injection to be performed at time $t=t_0$), the parameter $\alpha$ is the time integral of the model, and $\kappa$ is a local dispersion-related parameter. More precisely, the dispersion parameter $\kappa$ represents the local ratio at the detection site between squared carrier velocity $v^2$ (convection) and the dispersion coefficient D.

Once an intravascular indicator bolus is injected intravenously, its passage can be detected at each voxel within a defined region of interest (ROI) in order to generate a TCC for each ROI voxel. Each TCC is then fitted by the mLDRW model to estimate the parameter $\kappa$ and generate a parametric dispersion map. Intravascular dispersion has been shown to represent a better indicator than intravascular perfusion to detect the presence of angiogenesis and cancer. Preliminary results by DCE-US for PCa localization are in fact very promising. The dispersion parameter $\kappa$ is strongly affected by angiogenic variations in the microvascular architecture; these are reflected into the indicator multipath trajectories that determine the local dispersion kinetics.

Gadolinium Full Dispersion Model

In the presence of an extravascular indicator, such as gadolinium chelate, the leakage of the indicator must be taken into account as it provides a major contribution to the transport phenomenon and to the detected indicator concentration. The indicator concentration influencing the MR signal is the total concentration in tissue, C(t), in a given voxel. This can be expressed as $$C_t(t) = V_p C_p(t) + V_e C_e(t), \quad [3]$$

where $V_p$ is the fractional volume of intravascular blood plasma, $C_p$ is the intravascular concentration in blood plasma, $V_e$ is the fractional volume of the extravascular (and extracellular) space (interstitial space), and $C_e$ is the extravascular concentration. Using a simple monocompartment representation of leakage, with $1/K^{trans}$ representing the extravascular-leakage time constant, we can write $$V_e \frac{\partial C_e(t)}{\partial t} = K^{trans}(C_p(t) - C_e(t)). \quad [4]$$

After solving $C_e(t)$ from Eq. [4] with the initial conditions $C_p = C_e = 0$ for $t=0$, Eq. [3] can be rewritten as $$C_t(t) = V_p C_p(t) + K^{trans} \int_0^t C_p(\tau) e^{-k_{ep}(t-\tau)} d\tau, \quad [5]$$

with $k_{ep} = K^{trans}/V_e$.

The contributions of extravascular leakage and intravascular transport can be combined through the substitution of $C_p(t)$ in Eq. [4] by C(t) in Eq. [2]. The resulting dispersion model, referred to as full dispersion model (FDM), can then be formulated as $$C_t(t) = V_p \sqrt{\frac{\kappa}{2\pi(t-t_0)}} e^{-\frac{\kappa(t-t_0-\mu)^2}{2(t-t_0)}} + \alpha K^{trans} \int_{t_0}^{t-t_0} \sqrt{\frac{\kappa}{2\pi(\tau-t_0)}} e^{-\frac{\kappa(\tau-t_0-\mu)^2}{2(\tau-t_0)}} e^{-k_{ep}(t-(\tau-t_0))} d\tau. \quad [6]$$

Fitting Eq. [6] to measured TCCs enables the simultaneous estimation of the leakage parameter $k_{ep}$ and the dispersion parameter $\kappa$. Due to the unknown value of $\alpha$, $K^{trans}$ cannot be estimated and $k_{ep}$ is adopted to assess vascular permeability.

Gadolinium Reduced Dispersion Model

The contribution of the capillary compartment to the measured signal is often considered negligible 11. Under this assumption, $V_p \ll V_e$, $C_t(t) = V_e C_e(t)$, and Eq. [6] becomes $$C(t) = \alpha K^{trans} \int_{t_0}^{t-t_0} \sqrt{\frac{\kappa}{2\pi(\tau-t_0)}} e^{-\frac{\kappa(\tau-t_0-\mu)^2}{2(\tau-t_0)}} e^{-k_{ep}(t-(\tau-t_0))} d\tau. \quad [7]$$

Also the estimation of the model parameters in Eq. [7], referred to as reduced dispersion model (RDM), provides the simultaneous assessment of dispersion ($\kappa$) and vascular leakage ($k_{ep}$), characterizing vascular architecture and permeability, respectively. With respect to the model in Eq. [6], identification of the model in Eq. [7] reduces the number of parameters to be estimated from six to five. The same as for Eq. [6], $K^{trans}$ cannot be estimated.

Both models, FDM and RDM, include the AIF, which is given by the mLDRW model representing $C_p(t)$. As a result, a separate estimation of the AIF is not necessary. In general, for the standard leakage estimation by Eq. 4, assuming $V_p=0$ as in the Tofts model g, the AIF is either measured in a selected artery 11, or represented by a double exponent, $C_p(t) = \alpha_1 \exp(-m_1 t) - \alpha_2 \exp(-m_2 t)$, using a standard parameterization known per se from the literature [d,e].

Methods a. Data Acquisition

DCE MIl Imaging was performed with the following sequence parameters: repetition time of 50 ms, echo time of 3.9 ms, flip angle of 70 degrees, slice thickness of 4 mm, and pixel size of 1.67×1.67 mm$^2$. The resulting time resolution frame rate was 2 s (for 7 slices).

In addition to DCE MIl, only for validation purposes, a diffusion-weighted MIl was performed on the same slices to generate parametric ADC maps. T2 imaging was also performed for a better recognition of the anatomical structures.

FIG. 1 shows an example of T2, weighted-diffusion, and DCE MIl acquisition. All data were exported for further analysis in DICOM (Digital Imaging and Communications in Medicine) format.

b. Parameter Estimation

Based on the analysis of our data, the signal-to-noise ratio (SNR) in measured TCCs can be as low as few dBs. TCC SNR is assessed as 20 log 10(TCCpeak/σn), with TCC peak being the peak amplitude of the TCC and σn being the standard deviation of noise (difference between measured TCC and model fit). In order to deal with low SNR, a least-square procedure is implemented for curve fitting. In particular, because of the nonlinear fashion of the derived models, a nonlinear iterative fitting scheme is adopted. The search region space is confined in order to reduce the risk of convergence to local minima. To this end, the Trust-Region Reflective method is adopted.

Figure 2:
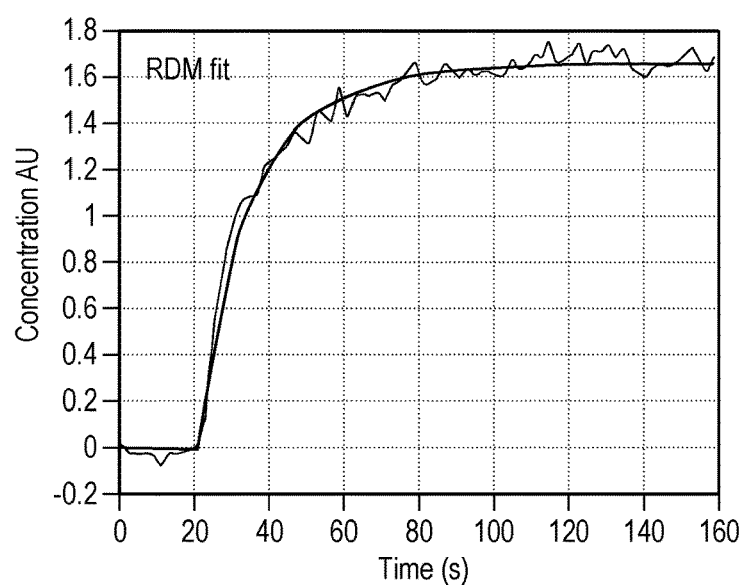
FIG. 2 shows measured TCC with RDM (left plot) and FDM (right plot) fits. The estimated, separate contributions of the intravascular (Cp(t)) and extravascular (Cp(t)) concentrations by FDM fitting are also shown.
Figure 2:
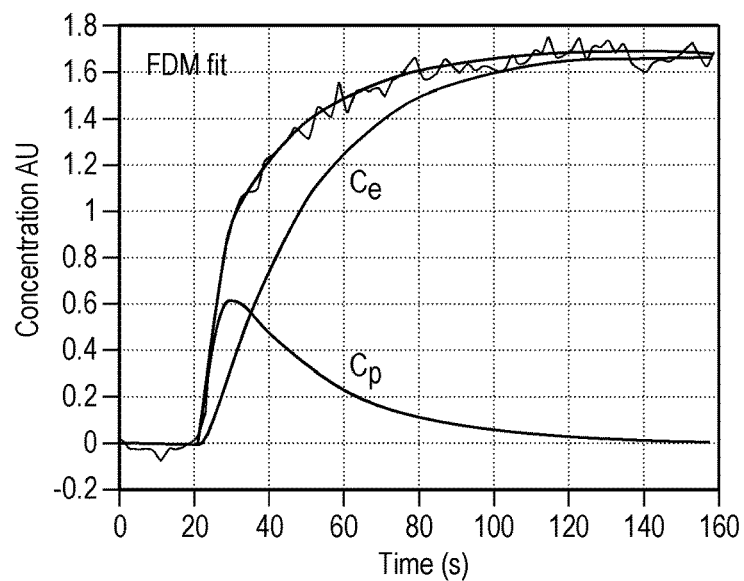

A number of search schemes were evaluated by dedicated simulations. For each parameterization representing measured data, 100 TCCs were generated by the proposed models and white Gaussian noise was added in order to achieve TCC SNR equal to 25 dB, representing the average SNR value for measurements in patients. The least squared error of the fit, as well as the fitting time, were the criteria used for evaluation of the fitting schemes. Eventually, the selected scheme combines a search grid with an iterative loop. In particular, in order to limit the number of parameters to be estimated in the iterative search loop, the theoretical injection time $t_0$ is estimated by a grid search. For each $t_0$ in a selected 12-s interval (until the indicator appearance time), with a resolution of 2 s, the Trust-Region Reflective search loop is performed. FIG. 2 shows an example of measured-TCC fit both by FDM and by RDM. By FDM fitting, being $V_p \neq 0$, the relative contributions of the intravascular, $C_p(t)$, and extravascular, $C_e(t)$, concentration can also be derived.

For analysis of the acquired data, a TCC must be fitted for each voxel covering the selected ROI. In order to reduce the convergence time and the risk of ending at local minima, the parameter initialization is based on the average estimates in the available dataset. After the parameters of interest, $k_{ep}$ and $\kappa$, are estimated at each voxel, a parametric map of permeability and dispersion can be generated. In order to assess the reliability of the estimated parameters, the correlation coefficient r of the obtained fits is derived for each voxel; TCC fits with r<0.85 are discarded. All the analysis is implemented in Matlab® (The MathWorks Inc., Natick, Mass.).

c. Validation

Figure 3B:
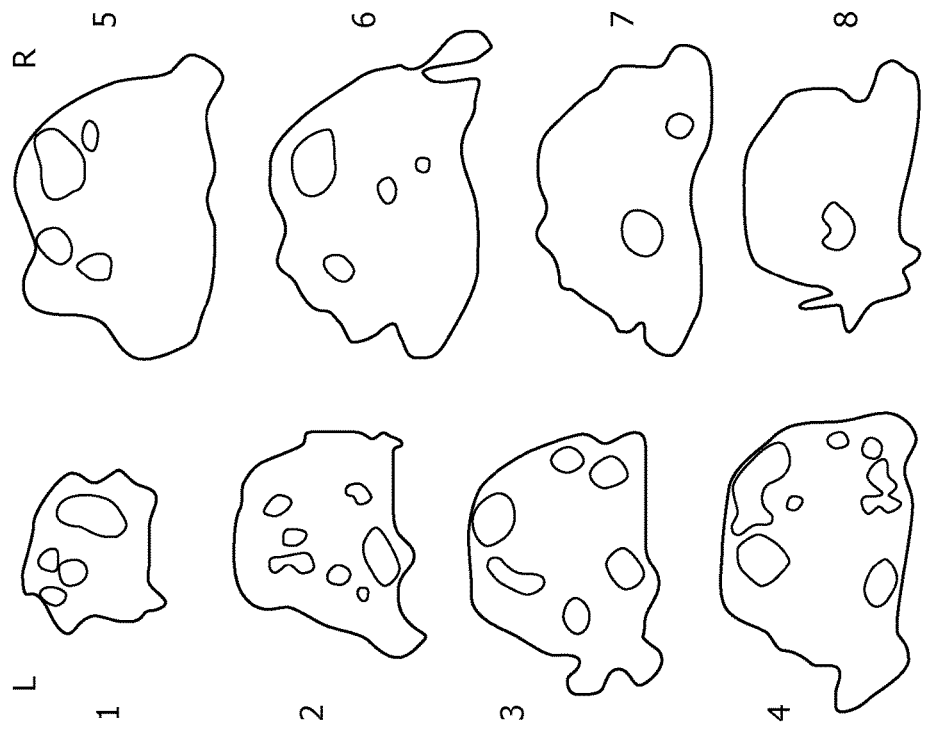
FIG. 3 shows examples of included (a) and excluded (b) histology, with the histology in (a) corresponding to FIG. 1.
Figure 3A:
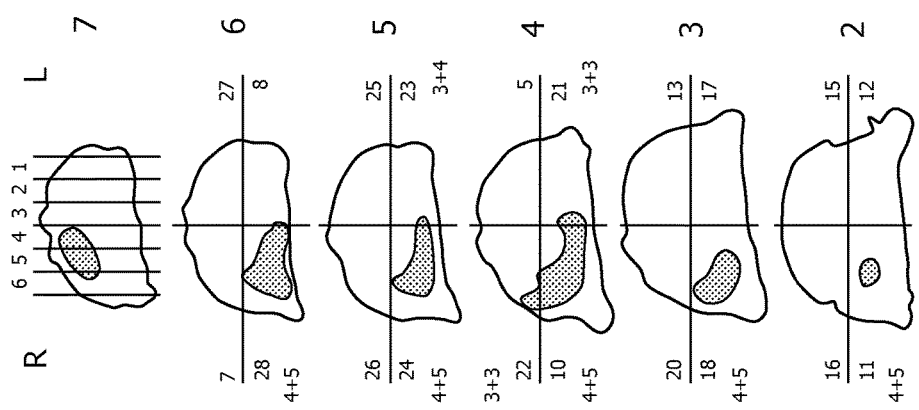

A preliminary validation was performed by comparison with the histological results after radical prostatectomy. After cutting the prostate in slices of 4-mm thickness, a pathologist analyzed them and marked the presence of PCa. PCa is associated with a decrease in cell differentiation, which is graded by the Gleason score. All of the histology slices were then scanned to generate digital images of the histology results. For each prostate, up to four slices were selected where large areas representing cancerous and healthy tissue could be clearly defined. From the scanned ten patients, three could not be included due to a scattered pathology result, unsuitable for validation purposes. A total number of 25 slices from seven patients were eventually analyzed and used for validation. FIG. 3a shows an example of included histology result, corresponding to corresponding to FIG. 1, while FIG. 3b shows an example of rejected (scattered) histology result.

Large ROIs ranging between 34 and 120 voxels were defined in each included slice, according to the histology, to mark cancerous and healthy tissue. The same ROIs where then overlapped on the corresponding parametric maps in order to assess the ability of the chosen parameter to detect PCa. The classification performance of each parameter was evaluated in terms of sensitivity, specificity, accuracy, and area under the receiver operating characteristic (ROC) curve. All the ROI voxels representing the class of healthy (about 1200 voxels) and cancerous tissue (about 1250 voxels) were used for this evaluation.

Figure 4:
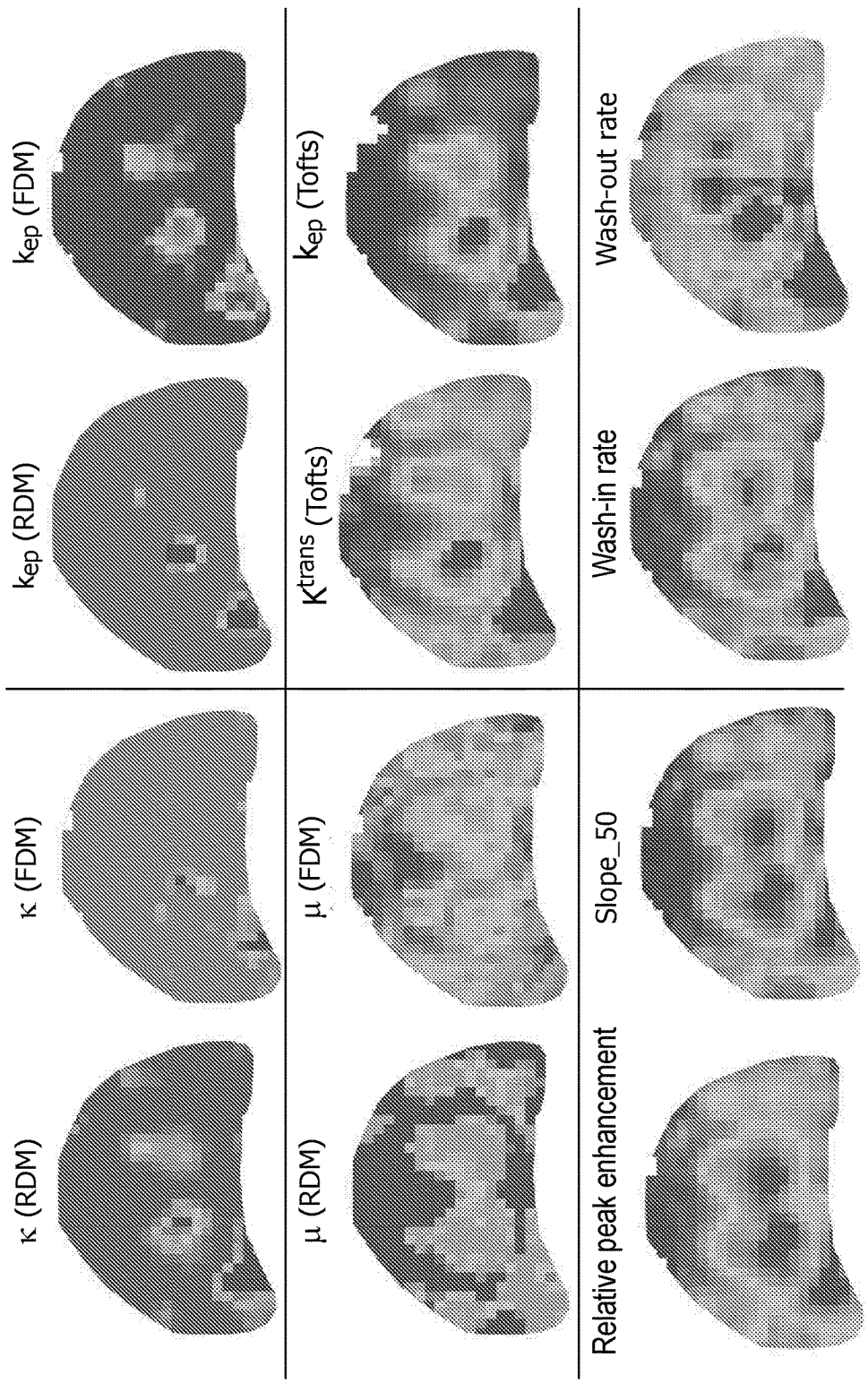
FIG. 4 shows Parametric maps corresponding to the scan in FIG. 1 and the histology in FIG. 3a and FIG. 5 shows Receiver Operating Characteristic (ROC) curves for the different parametric maps over the entire analyzed data set.

The evaluated parameters were ADC from diffusion-weighted MRI, $K^{trans}$ and $k_{ep}$ from the standard Tofts model, $\kappa$ and $k_{ep}$ from the FDM, and $\kappa$ and $k_{ep}$ from the RDM. The mean transit time parameter $\mu$, often adopted to assess intravascular perfusion by DCE-US 15, was also evaluated in order to compare the classification performance of perfusion with that of dispersion maps. The parameter $\mu$ was derived from both the FDM and the RDM. Additional empirical perfusion parameters, namely, wash-in rate, wash-out rate, peak enhancement, and slope_50 (slope within the first 50 s after contrast appearance), were also estimated. For the estimation of $K^{trans}$ and $k_{ep}$ from the standard Tofts model, the AIF was adopted based on the literature and modeled as a double exponential. FIG. 4 shows all the parametric maps corresponding to the histology in FIG. 3a and the acquisition in FIG. 1.

Results

According to our simulations with 25-dB SNR, the combination of a grid search on $t_0$ and the selected iterative search on the remaining parameters provides the best fitting results. The average convergence time for one curve fit was 3.5 s for RDM and 6 s for FDM, with a standard deviation in the $\kappa$ estimate of 30% for and 40%, respectively. The average correlation coefficient of the fits was 0.97±0.125.

Classification is evaluated at a voxel level in terms of sensitivity, specificity, accuracy, and ROC curve area. Classification by the dispersion parameter $\kappa$ was accurate, providing sensitivity=82.6, specificity=89.5, accuracy=86.0, and ROC area=0.91 for RDM, and sensitivity=72.4, specificity=81.4, accuracy=76.8, and ROC area=0.81 for FDM. All the classification results are reported in Table 1.

Figure 5:
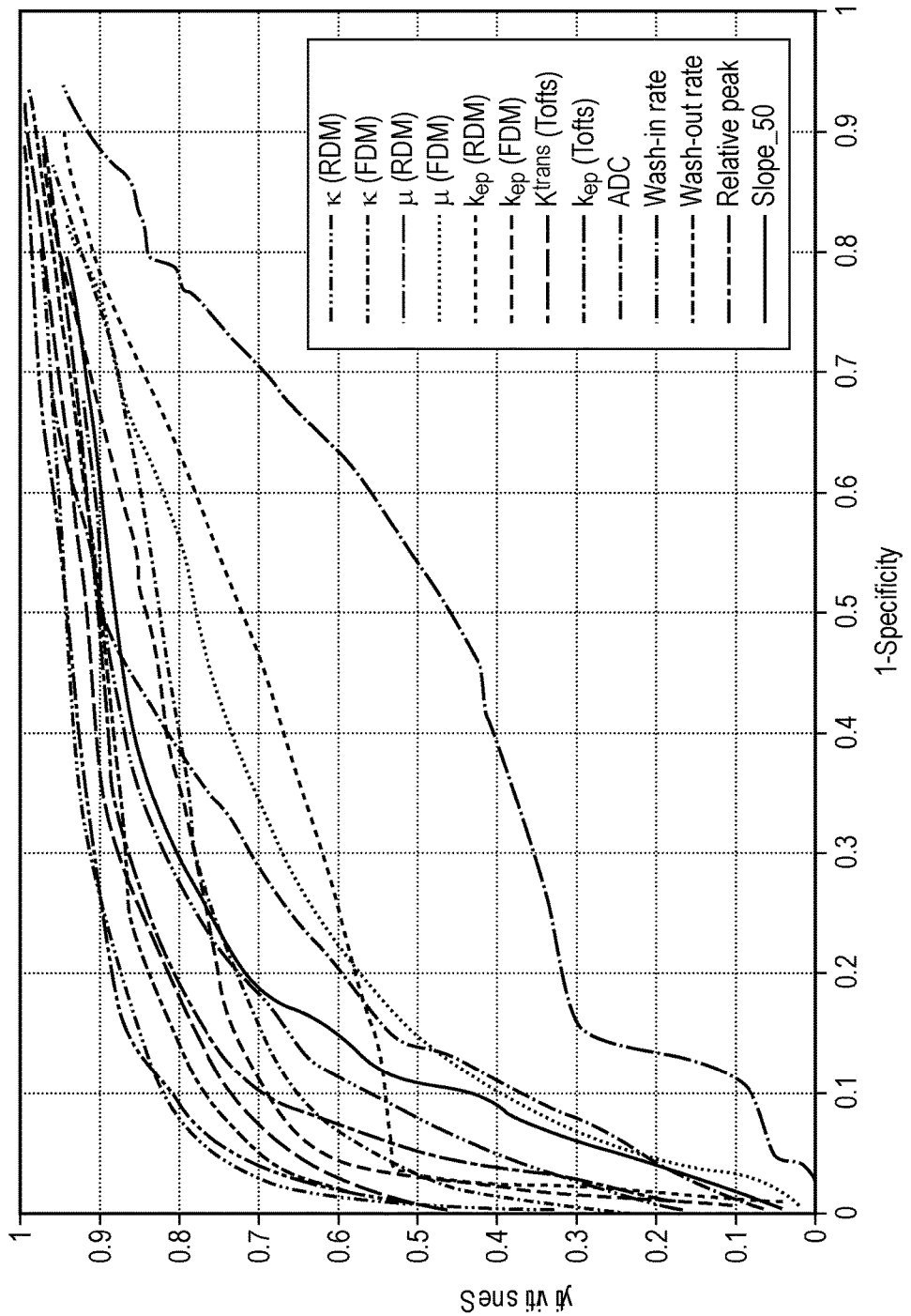

FIG. 5 shows the ROC curves for all the investigated methods.

TABLE 1

Classification results (sensitivity, specificity, accuracy, ROC area) for all the parameters

| Parameter | Sensitivity(%) | Specificity(%) | Accuracy(%) | ROC area |
|---|---|---|---|---|
| κ (RDM) | 82.6 | 89.5 | 86.0 | 0.91 |
| κ (FDM) | 72.4 | 81.4 | 76.8 | 0.81 |
| μ (RDM) | 61.2 | 43.7 | 53.0 | 0.52 |
| μ (FDM) | 63.9 | 74.0 | 68.9 | 0.72 |
| $k_{ep}$ (RDM) | 58.0 | 80.9 | 69.3 | 0.72 |
| $k_{ep}$ (FDM) | 72.0 | 86.4 | 79.1 | 0.82 |
| $K^{trans}$ (Tofts) | 79.7 | 83.1 | 81.5 | 0.88 |
| $k_{ep}$ (Tofts) | 85.3 | 85.3 | 85.3 | 0.91 |
| ADC | 69.7 | 71.8 | 70.7 | 0.78 |
| Wash-in rate | 76.7 | 76.1 | 76.4 | 0.81 |
| Wash-out rate | 80.5 | 85.7 | 83.1 | 0.88 |
| Peak enhancement | 75.1 | 82.6 | 78.6 | 0.82 |
| Slope_50 | 75.3 | 76.1 | 75.7 | 0.79 |

Only curve fits with r>0.85 were used to evaluate the classification performance of the method. The discarded curves were however only 1.5% of all the measured curves for FDM and RDM, and 8% for the standard Tofts model. The discarded curves are presented as white voxels in the images.

Discussion

A new DCE-MRI quantitative analysis method is proposed for the characterization of the microvascular architecture, aiming at detecting angiogenic changes related to cancer growth. The intravascular dispersion of an injected gadolinium-chelate bolus is estimated at each voxel and used to characterize the microvascular architecture. The dispersion kinetics of the agent is in fact related to the multipath trajectories of the contrast agent through the microvascular network. The resulting dispersion maps show accurate classification of cancer tissue as compared to histology.

Two models are proposed to describe the dispersion kinetics that are based on the combination of the Tofts compartmental model [f] to represent the leakage process and the solution of the convective dispersion equation proposed by Kuenen et al. [f] to represent the intravascular transport kinetics of the agent. A full dispersion model (FDM) and its reduced version (RDM), neglecting the intravascular contribution to the measured MR signal, are proposed. Both models permit the simultaneous estimation of the intravascular dispersion parameter κ and the leakage parameter kep.

The resulting dispersion maps, especially for the reduced model, produced classification results comparable with those obtained by the Tofts model (Ktrans, kep), and outperformed all the other parametric maps, including the ADC maps obtained by weighted-diffusion MRI.

The RDM outperformed the FDM in the classification performance by the estimated dispersion parameter κ and leakage parameter kep. Moreover, for both models, PCa classification by the simultaneously estimated parameter kep was less accurate than by the Tofts model. The reason can possibly reside in a dependency between the model parameters, resulting in unreliable estimates in the presence of low SNR. This has also been confirmed by our dedicated simulations, showing high standard deviation for the estimated parameters despite accurate curve fits (r=0.97).

Special attention is required for the parameter t0. According to Eqs [6] and [7], t0 could disappear from the model formulations by a simple variable substitution. Therefore, t0 should not be considered as part of the models. However, its estimation is necessary for TCC time translation prior to model fitting.

Compared with the application of Tofts model, the proposed method does not require the estimation of an AIF. This is a major advantage over other techniques, as the AIF estimation, introduced in, adds complexity to the measurement. In addition, the arbitrary choice of an ROI for the AIF measurement introduces a large degree of operator dependency in the final results. A general AIF can also be adopted based on a double exponential model and a general parameterization known per se from the literature[d,e]; however, this results in less accurate estimates of the kinetic parameters that will depend on the injection function and other patient-specific features influencing bolus transport and MR signal intensity 33.

In this invention, the parametric maps obtained by DCE-MRI as well as by weighted-diffusion MRI are compared with the corresponding histology slices. Slice selection is based on the known order and thickness of histology and MRI slices. This coarse comparison enables the validation of larger tumors only, which are consistently present in subsequent slices and show a clearly confined area. This enables defining regions on the parametric maps that are based on the histology and are covering with 100% confidence either cancerous or healthy tissue. Data where scattered cancer foci, marked by the pathologist, are not consistent through subsequent slices where excluded, as a reliable comparison was not feasible. In the future, this limitation could be overcome by employment of registration techniques that permit achieving accurate mapping between histology and MRI parametric maps. This should also take into account for prostate deformation due to the pressure exerted by the endorectal coil during the scan and for prostate deformation after radical prostatectomy due to gravity and fixation processes.

In the field of this invention, histology is considered as the ground truth for validation. However, while histology grading is based on the degree of cell differentiation (Gleason score) 30, the estimated dispersion map represents the characteristics of the microvascular architecture. In the future, comparison with immunohistological microvascular-density maps should therefore be considered.

REFERENCES a. Taylor, G., *Dispersion of soluble matter in solvent flowing slowly through a tube.* Proc. R. Soc. Lond, 1953. 219 (1137): p. 186-203.
b. Sheppard, C. W., *Basic principles of tracer methods: introduction to mathematical tracer kinetics.* first ed. 1962, New York: Wiley.
c. Mischi, M., *Contrast echocardiography for cardiac quantifications.* 2004, Eindhoven University of Technology: Eindhoven. Online: http://www.bmdresearch.com/db/files/23.pdf.
d. Tofts, P. S. and A. G. Kermode, *Measurement of the blood-brain barrier permeability and leakage space using dynamic MR imaging. 1. Fundamental concepts.* Magn Reson Med, 1991. 17(2): p. 357-67.
e. Parker, G. J., et al., *Experimentally-derived functional form for a population-averaged high-temporal-resolution arterial input function for dynamic contrast-enhanced MRI.* Magn Reson Med, 2006. 56(5): p. 993-1000.
f. Kuenen, M. P., M. Mischi, and H. Wijkstra, *Contrast-ultrasound diffusion imaging for localization of prostate cancer.* IEEE Trans Med Imaging, 2011. 30(8): p. 1493-502.
g. Vonken, E. J., et al., *Measurement of cerebral perfusion with dual-echo multi-slice quantitative dynamic susceptibility contrast MRI.* J Magn Reson Imaging, 1999. 10(2): p. 109-17.

The invention claimed is:

1. A computer implemented method of determining microvascular architecture, the method comprising:
    using a magnetic resonance imaging system, acquiring dynamic contrast-enhanced magnetic resonance data from a contrast agent administered to at least a part of a subject to be examined;
    simultaneously computing a leakage parameter ($k_{ep}$) and a dispersion parameter (κ) from the dynamic contrast-enhanced magnetic resonance data taking into account effects of both convective dispersion and extravasation kinetics of the contrast agent, wherein computing comprises:
        deriving a full dispersion model (FDM) or a reduced dispersion model (RDM) of intravascular and extravascular concentrations from a modified local density random walk model, and
        modeling convective dispersion by fitting a time concentration curve (TCC), that is measured from the magnetic resonance data, to the FDM or RDM of intravascular and extravascular concentrations,
        wherein the simultaneous computing does not include estimation or measurement of an arterial input function; and
    displaying parametric maps of the leakage parameter ($k_{ep}$) and the dispersion parameter (κ).

2. The method of claim 1, wherein the administered contrast agent's bolus' progression in the part of the subject is approximated by a normal (Gaussian) distribution.

3. The method of claim 1, wherein in the convective dispersion a capillary component is neglected.

4. The computer-implemented method of claim 1 wherein:
    in the extravasation kinetics, a monocomponent representation of leakage is employed.

5. The method of claim 4 wherein the leakage parameter ($k_{ep}$) is computed as a ratio of an extravascular-leakage time constant ($1/K^{trans}$) and a fractional volume of extravascular space ($V_e$).

6. The method of claim 1 wherein the leakage parameter ($k_{ep}$) is computed as a ratio of an extravascular-leakage time constant ($1/K^{trans}$) and a fractional volume of extravascular space ($V_e$).

7. A device to perform a method for determining microvascular architecture, the device comprising:
- a magnetic resonance imaging system operative to acquire dynamic contrast-enhanced magnetic resonance data from a contrast agent administered to at least a part of a subject to be examined;
- a computer programmed to simultaneously compute a leakage parameter ($k_{ep}$) and a dispersion parameter ($\kappa$) from the dynamic contrast-enhanced magnetic resonance data taking into account effects of both convective dispersion and extravasation kinetics of the contrast agent, wherein computing comprises:
  - deriving a reduced dispersion model (RDM) of intravascular and extravascular concentrations in which contribution of the capillary compartment to the magnetic resonance data is considered negligible from a modified local density random walk model,
  - modeling convective dispersion by fitting a time concentration curve (TCC), that is measured from the magnetic resonance data, to the RDM of intravascular and extravascular concentrations in which contribution of the capillary compartment to the magnetic resonance data is considered negligible, and
  - displaying parametric maps of at least one of the leakage parameter ($k_{ep}$) and the dispersion parameter ($\kappa$).

8. The device of claim 7 wherein a monocomponent representation of leakage is employed in the computing extravasation kinetics.

9. The device of claim 8 wherein the leakage parameter ($k_{ep}$) is computed as a ratio of an extravascular-leakage time constant ($1/K^{trans}$) and a fractional volume of extravascular space ($V_e$).

* * * * *